(12) United States Patent
Dunkel et al.

(10) Patent No.: US 7,868,179 B2
(45) Date of Patent: Jan. 11, 2011

(54) THIAZOLYL BIPHENYL AMIDES

(75) Inventors: Ralf Dunkel, Monheim (DE);
Hans-Ludwig Elbe, Wuppertal (DE);
Heiko Rieck, Ste Foy les Lyon (FR);
Ulrike Wahendorff-Neumann,
Neuwied (DE); Karl-Heinz Kuck,
Langenfeld (DE)

(73) Assignee: Bayer CropScience AG, Monheim (DE)

( * ) Notice: Subject to any disclaimer, the term of this patent is extended or adjusted under 35 U.S.C. 154(b) by 0 days.

(21) Appl. No.: 12/571,951

(22) Filed: Oct. 1, 2009

(65) Prior Publication Data

US 2010/0029730 A1   Feb. 4, 2010

Related U.S. Application Data

(63) Continuation of application No. 10/530,513, filed as application No. PCT/EP03/10758 on Sep. 26, 2003.

(30) Foreign Application Priority Data

Oct. 9, 2002  (DE) ................. 102 46 959

(51) Int. Cl.
*A01N 43/78* (2006.01)
*C07D 277/30* (2006.01)

(52) U.S. Cl. .................... 548/200; 514/365

(58) Field of Classification Search ........... 548/200
See application file for complete search history.

(56) References Cited

U.S. PATENT DOCUMENTS

| | | | |
|---|---|---|---|
| 5,922,732 A | 7/1999 | Urch et al. ......... | 514/304 |
| 5,968,947 A | 10/1999 | Urch et al. ......... | 514/299 |
| 6,093,726 A | 7/2000 | Urch et al. ......... | 514/299 |
| 6,174,894 B1 | 1/2001 | Urch et al. ......... | 514/299 |
| 6,177,442 B1 | 1/2001 | Urch et al. ......... | 514/299 |
| 6,207,676 B1 | 3/2001 | Urch et al. ......... | 514/304 |
| 6,291,474 B1 | 9/2001 | Brightwell et al. ........ | 514/299 |
| 6,391,883 B1 | 5/2002 | Urch et al. ......... | 514/255 |
| 6,573,275 B1 | 6/2003 | Urch et al. ......... | 514/304 |
| 7,388,097 B2 | 6/2008 | Elbe et al. | |
| 2002/0061913 A1 | 5/2002 | Urch et al. ......... | 514/366 |
| 2006/0128769 A1 | 6/2006 | Dunkel et al. | |
| 2007/0060579 A1 | 3/2007 | Wachendorff-Neumann et al. | |
| 2007/0082877 A1 | 4/2007 | Dunkel et al. | |
| 2008/0064874 A1 | 3/2008 | Dunkel et al. | |
| 2008/0242708 A1 | 10/2008 | Dunkel et al. | |
| 2009/0076113 A1 | 3/2009 | Dunkel et al. | |
| 2009/0105316 A1 | 4/2009 | Dunkel et al. | |
| 2009/0118346 A1 | 5/2009 | Dunkel et al. | |
| 2009/0286681 A1 | 11/2009 | Dahmen et al. | |
| 2010/0056786 A1 | 3/2010 | Straub | |

FOREIGN PATENT DOCUMENTS

| | | |
|---|---|---|
| CA | 2474902 A1 * | 8/2003 |
| DE | 102 04 391 | 8/2003 |
| EP | 0 545 099 | 6/1993 |
| JP | 08/176112 A * | 7/1996 |
| JP | 9-132567 | 5/1997 |
| WO | 02059086 | 8/2002 |

OTHER PUBLICATIONS

An English translation of JP 08/176112, 1996.*
Bull. Korean Chem. Soc., vol. 21, No. 2, (month unavailable) 2000, pp. 165-166, Nakcheol Jeong et al, "A Facile Preparation of the Fluoroaryl Zinc Halides: an Application to the Synthesis of Diflunisal".
Chem. Pharm. Bull., 40(1), (month unavailable) 1992, pp. 240-244, Kiyoshi Taniguchi et al, "New 2-Aryliminoimidazolidines. II. Synthesis and Antihypertensive Activity of 2-(Biphenylimino)-imidazolidines".
Office Action mailed Sep. 21, 2006, in U.S. Appl. No. 10/530,513, Dunkel et al., filed Aug. 22, 2005.
Office Action mailed May 9, 2007, in U.S. Appl. No. 10/530,513, Dunkel et al., filed Aug. 22, 2005.
Office Action mailed Nov. 16, 2007, in U.S. Appl. No. 10/530,513, Dunkel et al., filed Aug. 22, 2005.
Office Action mailed Sep. 9, 2008, in U.S. Appl. No. 10/530,513, Dunkel et al., filed Aug. 22, 2005.
Office Action (Advisory Action) mailed Nov. 18, 2008, in U.S. Appl. No. 10/530,513, Dunkel et al., filed Aug. 22, 2005.
Office Action mailed Jun. 10, 2009, in U.S. Appl. No. 10/530,513, Dunkel et al., filed Aug. 22, 2005.
Office Action (Advisory Action) mailed Sep. 21, 2009, in U.S. Appl. No. 10/530,513, Dunkel et al., filed Aug. 22, 2005.
Office Action mailed Dec. 29, 2009, in U.S. Appl. No. 10/530,513, Dunkel et al., filed Aug. 22, 2005.

(Continued)

*Primary Examiner*—Laura L. Stockton
(74) *Attorney, Agent, or Firm*—Sterne, Kessler, Goldstein & Fox P.L.L.C.

(57) ABSTRACT

The invention relates to novel thiazolylbiphenylamides of the formula (I)

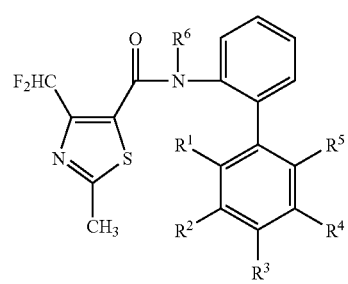

in which $R^1$, $R^2$, $R^3$, $R^4$, $R^5$ and $R^6$ are as defined in the disclosure, to a process for preparing these compounds and to their use for controlling unwanted micro-organisms.

13 Claims, No Drawings

OTHER PUBLICATIONS

Office Action mailed Dec. 23, 2009, in U.S. Appl. No. 12/097,753, Dunkel et al., filed Nov. 3, 2008.

Office Action mailed Feb. 17, 2010, in U.S. Appl. No. 11/661,092, Dunkel et al., filed Oct. 8, 2008.

Notice of Allowance (Notice of Allowability) mailed Feb. 26, 2008, in U.S. Appl. No. 10/502,994, Elbe et al., filed Jan. 31, 2005.

International Search Report for International Application No. PCT/EP2003/010758, European Patent Office, Netherlands, mailed on Apr. 7, 2004.

* cited by examiner

THIAZOLYL BIPHENYL AMIDES

This application is a continuation of U.S. application Ser. No. 10/530,513, filed Aug. 22, 2005, which was filed under 35 U.S.C. 371 as a national stage application of PCT/EP2003/010758, filed Sep. 26, 2003, which was published in German as International Patent Publication WO 2004/035555 on Apr. 29, 2004, and is entitled to the right of priority of German Patent Application 102 46 959.8, filed Oct. 9, 2002.

The present invention relates to novel thiazolylbiphenylamides, to a plurality of processes for their preparation and to their use for controlling harmful microorganisms in crop protection and in the protection of materials.

It is already known that numerous carboxanilides have fungicidal properties (compare, for example, EP 0 545 099). The activity of the compounds described therein is good; however, at low application rates it is sometimes unsatisfactory.

This invention now provides novel thiazolylbiphenylamides of the formula (I)

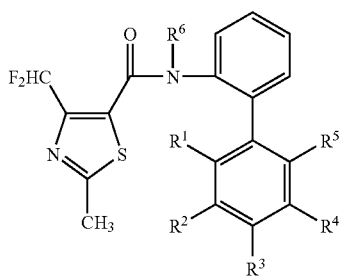

(I)

in which $R^1$, $R^2$, $R^3$, $R^4$ and $R^5$ independently of one another represent hydrogen, halogen, cyano, nitro, $C_1$-$C_6$-alkyl, $C_2$-$C_6$-alkenyl, $C_1$-$C_4$-alkoxy, $C_1$-$C_4$-alkylthio, $C_1$-$C_4$-alkylsulfonyl, $C_3$-$C_6$-cycloalkyl, or represent $C_1$-$C_4$-haloalkyl, $C_1$-$C_4$-haloalkoxy, $C_1$-$C_4$-haloalkylthio or $C_1$-$C_4$-haloalkylsulfonyl having in each case 1 to 5 halogen atoms, $R^1$ and $R^2$ or $R^2$ and $R^3$ furthermore together represent optionally halogen- or $C_1$-$C_6$-alkyl-substituted alkenylene, $R^6$ represents $C_1$-$C_8$-alkyl, $C_1$-$C_6$-alkylsulfinyl, $C_1$-$C_6$-alkylsulfonyl, $C_1$-$C_4$-alkoxy-$C_1$-$C_4$-alkyl, $C_3$-$C_8$-cycloalkyl; $C_1$-$C_6$-haloalkyl, $C_1$-$C_4$-haloalkylsulfanyl, $C_1$-$C_4$-haloalkylsulfinyl, $C_1$-$C_4$-haloalkylsulfonyl, halo-$C_1$-$C_4$-alkoxy-$C_1$-$C_4$-alkyl, $C_3$-$C_8$-halocycloalkyl having in each case 1 to 9 fluorine, chlorine and/or bromine atoms; —$COR^7$, —$CONR^8R^9$ or —$CH_2NR^{10}R^{11}$, $R^7$ represents hydrogen, $C_1$-$C_8$-alkyl, $C_1$-$C_8$-alkoxy, $C_1$-$C_4$-alkoxy-$C_1$-$C_4$-alkyl, $C_3$-$C_8$-cycloalkyl; $C_1$-$C_6$-haloalkyl, $C_1$-$C_6$-haloalkoxy, halo-$C_1$-$C_4$-alkoxy-$C_1$-$C_4$-alkyl, $C_3$-$C_8$-halocycloalkyl having in each case 1 to 9 fluorine, chlorine and/or bromine atoms, or 4-(difluoromethyl)-2-methyl-1,3-thiazol-2-yl, $R^8$ and $R^9$ independently of one another represent hydrogen, $C_1$-$C_8$-alkyl, $C_1$-$C_4$-alkoxy-$C_1$-$C_4$-alkyl, $C_3$-$C_8$-cycloalkyl; $C_1$-$C_8$-haloalkyl, halo-$C_1$-$C_4$-alkoxy-$C_1$-$C_4$-alkyl, $C_3$-$C_8$-halocycloalkyl having in each case 1 to 9 fluorine, chlorine and/or bromine atoms, $R^8$ and $R^9$ furthermore together with the nitrogen atom to which they are attached form a saturated heterocycle which is optionally mono- or polysubstituted by identical or different substituents from the group consisting of halogen and $C_1$-$C_4$-alkyl and which has 5 to 8 ring atoms, where the heterocycle may contain 1 or 2 further non-adjacent heteroatoms from the group consisting of oxygen, sulfur and $NR^{12}$, $R^{10}$ and $R^{11}$ independently of one another represent hydrogen, $C_1$-$C_8$-alkyl, $C_3$-$C_8$-cycloalkyl; $C_1$-$C_8$-haloalkyl, $C_3$-$C_8$-halocycloalkyl having in each case 1 to 9 fluorine, chlorine and/or bromine atoms, $R^{10}$ and $R^{11}$ furthermore together with the nitrogen atom to which they are attached form a saturated heterocycle which is optionally mono- or polysubstituted by identical or different substituents from the group consisting of halogen and $C_1$-$C_4$-alkyl and which has 5 to 8 ring atoms, where the heterocycle may contain 1 or 2 further non-adjacent heteroatoms from the group consisting of oxygen, sulfur and $NR^{12}$, $R^{12}$ represents hydrogen or $C_1$-$C_6$-alkyl.

Furthermore, it has been found that thiazolylbiphenylamides of the formula (I) are obtained when (A) thiazolylbiphenylamides of the formula (II)

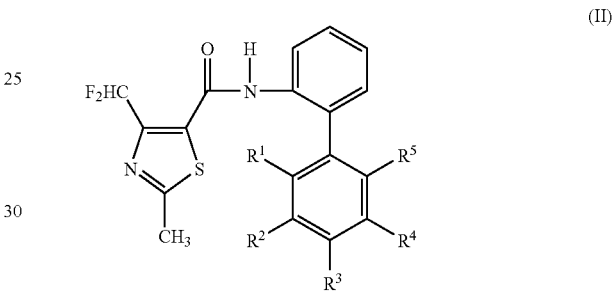

(II)

in which $R^1$, $R^2$, $R^3$, $R^4$ and $R^5$ are as defined above, are reacted with a halide of the formula (III)

$$R^6\text{—}X \qquad (III)$$

in which $R^6$ is as defined above and

X represents chlorine, bromine or iodine in the presence of a base and in the presence of a diluent.

Finally, it has been found that the novel thiazolylbiphenylamides of the formula (I) have very good microbicidal properties and can be used for controlling unwanted microorganisms both in crop protection and in the protection of materials.

Surprisingly, the thiazolylbiphenylamides of the formula (I) according to the invention have considerably better fungicidal activity than the constitutionally most similar active compounds of the prior art having the same direction of action.

The formula (I) provides a general definition of the thiazolylbiphenylamides according to the invention. Preferred definitions of the substituents mentioned in the formulae above and below are given below. They also apply to the precursors and intermediates.

$R^1$, $R^2$, $R^3$, $R^4$ and $R^5$ independently of one another preferably represent hydrogen, fluorine, chlorine, bromine, cyano, nitro, methyl, ethyl, n- or isopropyl, n-, iso-, sec- or tert-butyl, methoxy, ethoxy, methylthio, ethylthio, n- or isopropylthio, cyclopropyl, trifluoromethyl, trichloromethyl, trifluoroethyl, difluoromethoxy, trifluoromethoxy, difluorochloromethoxy, trifluoroethoxy, difluoromethylthio, difluorochloromethylthio or trifluoromethylthio.

$R^1$ and $R^2$ or $R^2$ and $R^3$ furthermore together preferably represent optionally fluorine-, chlorine-, bromine- or methyl-substituted butadienediyl.

$R^6$ preferably represents $C_1$-$C_6$-alkyl, $C_1$-$C_4$-alkylsulfinyl, $C_1$-$C_4$-alkylsulfonyl, $C_1$-$C_3$-alkoxy-$C_1$-$C_3$-alkyl, $C_3$-$C_6$-cycloalkyl; $C_1$-$C_4$-haloalkyl, $C_1$-$C_4$-haloalkylsulfanyl, $C_1$-$C_4$-haloalkylsulfinyl, $C_1$-$C_4$-haloalkylsulfonyl, halo-$C_1$-$C_3$-alkoxy-$C_1$-$C_3$-alkyl, $C_3$-$C_6$-halocycloalkyl having in each case 1 to 9 fluorine, chlorine and/or bromine atoms; —$COR^7$, —$CONR^8R^9$ or —$CH_2NR^{10}R^{11}$.

$R^7$ preferably represents hydrogen, $C_1$-$C_6$-alkyl, $C_1$-$C_4$-alkoxy, $C_1$-$C_3$-alkoxy-$C_1$-$C_3$-alkyl, $C_3$-$C_6$-cycloalkyl; $C_1$-$C_4$-haloalkyl, $C_1$-$C_4$-haloalkoxy, halo-$C_1$-$C_3$-alkoxy-$C_1$-$C_3$-alkyl, $C_3$-$C_6$-halocycloalkyl having in each case 1 to 9 fluorine, chlorine and/or bromine atoms or 4-(difluoromethyl)-2-methyl-1,3-thiazol-2-yl.

$R^8$ and $R^9$ independently of one another preferably represent hydrogen, $C_1$-$C_6$-alkyl, $C_1$-$C_3$-alkoxy-$C_1$-$C_3$-alkyl, $C_3$-$C_6$-cycloalkyl; $C_1$-$C_4$-haloalkyl, halo-$C_1$-$C_3$-alkoxy-$C_1$-$C_3$-alkyl, $C_3$-$C_6$-halocycloalkyl having in each case 1 to 9 fluorine, chlorine and/or bromine atoms.

$R^8$ and $R^9$ furthermore together with the nitrogen atom to which they are attached preferably form a saturated heterocycle which is optionally mono- to tetrasubstituted by identical or different substituents from the group consisting of halogen and $C_1$-$C_4$-alkyl and which has 5 to 8 ring atoms, where the heterocycle may contain 1 or 2 further non-adjacent heteroatoms from the group consisting of oxygen, sulfur and $NR^{12}$.

$R^{10}$ and $R^{11}$ independently of one another preferably represent hydrogen, $C_1$-$C_6$-alkyl, $C_3$-$C_6$-cycloalkyl; $C_1$-$C_4$-haloalkyl, $C_3$-$C_6$-halocycloalkyl having in each case 1 to 9 fluorine, chlorine and/or bromine atoms.

$R^{10}$ and $R^{11}$ furthermore together with the nitrogen atom to which they are attached preferably form a saturated heterocycle which is optionally mono- or polysubstituted by identical or different substituents from the group consisting of halogen and $C_1$-$C_4$-alkyl and which has 5 to 8 ring atoms, where the heterocycle may contain 1 or 2 further non-adjacent heteroatoms from the group consisting of oxygen, sulfur and $NR^{12}$.

$R^{12}$ preferably represents hydrogen or $C_1$-$C_4$-alkyl.

$R^1$, $R^2$, $R^3$, $R^4$ and $R^5$ independently of one another particularly preferably represent hydrogen, fluorine, chlorine, bromine, cyano, methyl, methoxy, methylthio, trifluoromethyl, difluoromethoxy, trifluoromethoxy, difluoromethylthio or trifluoromethylthio.

$R^6$ particularly preferably represents methyl, ethyl, n- or isopropyl, n-, iso-, sec- or tert-butyl, pentyl or hexyl, methylsulfinyl, ethylsulfinyl, n- or isopropylsulfinyl, n-, iso-, sec- or tert-butylsulfinyl, methylsulfonyl, ethylsulfonyl, n- or isopropylsulfonyl, n-, iso-, sec- or tert-butylsulfonyl, methoxymethyl, methoxyethyl, ethoxymethyl, ethoxyethyl, cyclopropyl, cyclopentyl, cyclohexyl, trifluoromethyl, trichloromethyl, trifluoroethyl, difluoromethylsulfanyl, difluorochloromethylsulfanyl, trifluoromethylsulfanyl, trifluoromethylsulfinyl, trifluoromethylsulfonyl, trifluoromethoxymethyl; —$COR^7$, —$CONR^8R^9$ or —$CH_2NR^{10}R^{11}$.

$R^7$ particularly preferably represents hydrogen, methyl, ethyl, n- or isopropyl, tert-butyl, methoxy, ethoxy, tert-butoxy, cyclopropyl; trifluoromethyl, trifluoromethoxy or 4-(difluoromethyl)-2-methyl-1,3-thiazol-2-yl.

$R^8$ and $R^9$ independently of one another particularly preferably represent hydrogen, methyl, ethyl, n- or isopropyl, n-, iso-, sec- or tert-butyl, methoxymethyl, methoxyethyl, ethoxymethyl, ethoxyethyl, cyclopropyl, cyclopentyl, cyclohexyl; trifluoromethyl, trichloromethyl, trifluoroethyl, trifluoromethoxymethyl, $R^8$ and $R^9$ furthermore together with the nitrogen atom to which they are attached particularly preferably form a saturated heterocycle from the group consisting of morpholine, thiomorpholine and piperazine, which heterocycle is optionally mono- to tetrasubstituted by identical or different substituents from the group consisting of fluorine, chlorine, bromine and methyl, where the piperazine may be substituted on the second nitrogen atom by $R^{12}$, $R^{10}$ and $R^{11}$ independently of one another particularly preferably represent hydrogen, methyl, ethyl, n- or isopropyl, n-, iso-, sec- or tert-butyl, methoxymethyl, methoxyethyl, ethoxymethyl, ethoxyethyl, cyclopropyl, cyclopentyl, cyclohexyl; trifluoromethyl, trichloromethyl, trifluoroethyl, trifluoro-methoxymethyl, $R^{10}$ and $R^{11}$ furthermore together with the nitrogen atom to which they are attached particularly preferably form a saturated heterocycle from the group consisting of morpholine, thiomorpholine and piperazine, which heterocycle is optionally mono- to tetrasubstituted by identical or different substituents from the group consisting of fluorine, chlorine, bromine and methyl, where the piperazine may be substituted on the second nitrogen atom by $R^{12}$, $R^{12}$ particularly preferably represents hydrogen, methyl, ethyl, n- or isopropyl, n-, iso-, sec- or tert-butyl.

Very particular preference is given to thiazolylbiphenylamides of the formula (I) in which in each case four of the radicals $R^1$, $R^2$, $R^3$, $R^4$ and $R^5$ represent hydrogen.

Very particular preference is given to thiazolylbiphenylamides of the formula (I) in which $R^1$, $R^2$, $R^4$ and $R^5$ each represent hydrogen and $R^3$ is as defined above.

Very particular preference is given to thiazolylbiphenylamides of the formula (I) in which $R^1$, $R^2$, $R^4$ and $R^5$ each represent hydrogen and $R^3$ represents fluorine, chlorine, bromine, methyl, trifluoromethyl, trifluoromethoxy or trifluoromethylthio.

Very particular preference is given to thiazolylbiphenylamides of the formula (I) in which $R^2$, $R^4$ and $R^5$ each represent hydrogen and $R^1$ and $R^3$ independently of one another are as defined above.

Very particular preference is given to thiazolylbiphenylamides of the formula (I) in which $R^2$, $R^4$ and $R^5$ each represent hydrogen and $R^1$ and $R^3$ independently of one another represent fluorine, chlorine, bromine, methyl or trifluoromethyl.

Very particular preference is given to thiazolylbiphenylamides of the formula (I) in which $R^1$, $R^4$ and $R^5$ each represent hydrogen and $R^2$ and $R^3$ independently of one another are as defined above.

Very particular preference is given to thiazolylbiphenylamides of the formula (I) in which $R^1$, $R^4$ and $R^5$ each represent hydrogen and $R^2$ and $R^3$ independently of one another represent fluorine, chlorine, bromine, methyl or trifluoromethyl.

Very particular preference is given to thiazolylbiphenylamides of the formula (I) in which $R^1$, $R^3$ and $R^5$ each represent hydrogen and $R^2$ and $R^4$ independently of one another have the meanings given above.

Very particular preference is given to thiazolylbiphenylamides of the formula (I), in which
$R^1$, $R^3$ and $R^5$ each represent hydrogen and
$R^2$ and $R^4$ independently of one another represent fluorine, chlorine, bromine, methyl or trifluoromethyl.

Very particular preference is given to thiazolylbiphenylamides of the formula (I) in which
$R^6$ represents —$COR^7$ and $R^7$ represents 4-(difluoromethyl)-2-methyl-1,3-thiazol-2-yl.

Very particular preference is given to thiazolylbiphenylamides of the formula (I) in which
$R^6$ represents —$COR^7$ and $R^7$ represents methyl, ethyl, cyclopropyl or trifluoromethyl, in particular methyl.

Very particular preference is given to thiazolylbiphenylamides of the formula (I) in which
$R^6$ represents —CHO.

Very particular preference is given to thiazolylbiphenylamides of the formula (I) in which
$R^6$ represents methyl, ethyl, n- or isopropyl, n-, iso-, sec- or tert-butyl, methylsulfinyl, methylsulfonyl, methoxymethyl, ethoxyethyl, cyclopropyl, cyclopentyl, cyclohexyl, trifluoromethyl, trichloromethyl, trifluoromethylsulfanyl, trifluoromethylsulfinyl, trifluoromethylsulfonyl, trifluoromethoxymethyl, in particular methyl, isopropyl or cyclopropyl.

A preferred group are thiazolylbiphenylamides of the formula (I-a)

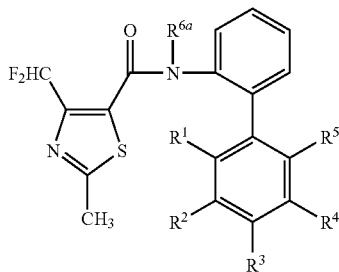

(I-a)

in which
$R^1$, $R^2$, $R^3$, $R^4$ and $R^5$ independently of one another represent hydrogen, halogen, cyano, nitro, $C_1$-$C_6$-alkyl, $C_2$-$C_6$-alkenyl, $C_1$-$C_4$-alkoxy, $C_1$-$C_4$-alkylthio, $C_1$-$C_4$-alkylsulfonyl, $C_3$-$C_6$-cycloalkyl, or represent $C_1$-$C_4$-haloalkyl, $C_1$-$C_4$-haloalkoxy, $C_1$-$C_4$-haloalkylthio or $C_1$-$C_4$-haloalkylsulfonyl having in each case 1 to 5 halogen atoms, $R^1$ and $R^2$ or $R^2$ and $R^3$ furthermore together represent optionally halogen- or $C_1$-$C_6$-alkyl-substituted alkenylene, $R^{6a}$ represents $C_1$-$C_8$-alkyl, $C_1$-$C_6$-alkylsulfinyl, $C_1$-$C_6$-alkylsulfonyl, $C_1$-$C_4$-alkoxy-$C_1$-$C_4$-alkyl, $C_3$-$C_8$-cycloalkyl; $C_1$-$C_6$-haloalkyl, $C_1$-$C_4$-haloalkylsulfanyl, $C_1$-$C_4$-haloalkylsulfinyl, $C_1$-$C_4$-haloalkylsulfonyl, halo-$C_1$-$C_4$-alkoxy-$C_1$-$C_4$-alkyl, $C_3$-$C_8$-halocycloalkyl having in each case 1 to 9 fluorine, chlorine and/or bromine atoms; —$COR^{7a}$, —$CONR^8R^9$ or —$CH_2NR^{10}R^{11}$, $R^{7a}$ represents hydrogen, $C_3$-$C_8$-cycloalkyl; $C_3$-$C_8$-halocycloalkyl having in each case 1 to 9 fluorine, chlorine and/or bromine atoms or 4-(difluoromethyl)-2-methyl-1,3-thiazol-2-yl, $R^8$ and $R^9$ independently of one another represent hydrogen, $C_1$-$C_8$-alkyl, $C_1$-$C_4$-alkoxy-$C_1$-$C_4$-alkyl, $C_3$-$C_8$-cycloalkyl; $C_1$-$C_8$-haloalkyl, halo-$C_1$-$C_4$-alkoxy-$C_1$-$C_4$-alkyl, $C_3$-$C_8$-halocycloalkyl having in each case 1 to 9 fluorine, chlorine and/or bromine atoms, $R^8$ and $R^9$ furthermore together with the nitrogen atom to which they are attached form a saturated heterocycle which is optionally mono- or polysubstituted by identical or different substituents from the group consisting of halogen and $C_1$-$C_4$-alkyl and which has 5 to 8 ring atoms, where the heterocycle may contain 1 or 2 further non-adjacent heteroatoms from a group consisting of oxygen, sulfur and $NR^{12}$, $R^{10}$ and $R^{11}$ independently of one another represent hydrogen, $C_1$-$C_8$-alkyl, $C_3$-$C_8$-cycloalkyl; $C_1$-$C_8$-haloalkyl, $C_3$-$C_8$-halocycloalkyl having in each case 1 to 9 fluorine, chlorine and/or bromine atoms, $R^{10}$ and $R^{11}$ furthermore together with the nitrogen atom to which they are attached form a saturated heterocycle which is optionally mono- or polysubstituted by identical or different substituents from the group consisting of halogen and $C_1$-$C_4$-alkyl and which has 5 to 8 ring atoms, where the heterocycle may contain 1 or 2 further non-adjacent heteroatoms from a group consisting of oxygen, sulfur and $NR^{12}$, $R^{12}$ represents hydrogen or $C_1$-$C_6$-alkyl.

Formula (I-a) provides a general definition of the thiazolylbiphenylamides according to the invention. Preferred definitions of the substituents mentioned in this formula are given below.

$R^1$, $R^2$, $R^3$, $R^4$, $R^5$, $R^8$, $R^9$, $R^{10}$, $R^{11}$ and $R^{12}$ independently of one another preferably, particularly preferably and very particularly preferably have those meanings which have already been mentioned in connection with the description of the compounds of the formula (I) according to the invention as being preferred, particularly preferred and very particularly preferred, respectively, for these radicals.

$R^{6a}$ preferably represents $C_1$-$C_6$-alkyl, $C_1$-$C_4$-alkylsulfinyl, $C_1$-$C_4$-alkylsulfonyl, $C_1$-$C_3$-alkoxy-$C_1$-$C_3$-alkyl, $C_3$-$C_6$-cycloalkyl; $C_1$-$C_4$-haloalkyl, $C_1$-$C_4$-haloalkylsulfanyl, $C_1$-$C_4$-haloalkylsulfinyl, $C_1$-$C_4$-haloalkylsulfonyl, halo-$C_1$-$C_3$-alkoxy-$C_1$-$C_3$-alkyl, $C_3$-$C_6$-halocycloalkyl having in each case 1 to 9 fluorine, chlorine and/or bromine atoms; —$COR^{7a}$, —$CONR^8R^9$ or —$CH_2NR^{10}R^{11}$.

$R^{7a}$ preferably represents hydrogen, $C_3$-$C_6$-cycloalkyl; $C_3$-$C_6$-halocycloalkyl having in each case 1 to 9 fluorine, chlorine and/or bromine atoms or 4-(difluoromethyl)-2-methyl-1,3-thiazol-2-yl.

$R^{6a}$ particularly preferably represents methyl, ethyl, n- or isopropyl, n-, iso-, sec- or tert-butyl, pentyl or hexyl, methylsulfinyl, ethylsulfinyl, n- or isopropylsulfinyl, n-, iso-, sec- or tert-butylsulfinyl, methylsulfonyl, ethylsulfonyl, n- or isopropylsulfonyl, n-, iso-, sec- or tert-butylsulfonyl, methoxymethyl, methoxyethyl, ethoxymethyl, ethoxyethyl, cyclopropyl, cyclopentyl, cyclohexyl, trifluoromethyl, trichloromethyl, trifluoroethyl, difluoromethylsulfanyl, difluorochloromethylsulfanyl, trifluoromethylsulfanyl, trifluoromethylsulfinyl, trifluoromethylsulfonyl, trifluoromethoxymethyl; —$COR^{7a}$, —$CONR^8R^9$ or —$CH_2NR^{10}R^{11}$.

$R^7$ particularly preferably represents hydrogen, cyclopropyl or 4-(difluoromethyl)-2-methyl-1,3-thiazol-2-yl.

Preference is furthermore given to thiazolylbiphenylamides of the formula (I-a) in which $R^1$, $R^2$, $R^3$, $R^4$ and $R^5$ do not all represent hydrogen.

Preference is furthermore given to thiazolylbiphenylamides of the formula (I-a) in which $R^1$, $R^2$, $R^3$, $R^4$ and $R^5$ have the meanings given above, but do not represent halogen.

Preference is furthermore given to thiazolylbiphenylamides of the formula (I-a) in which $R^1$, $R^2$, $R^3$, $R^4$ and $R^5$ do not all represent hydrogen and furthermore independently of one another do not represent halogen.

Using N-(4'-bromo-1,1'-biphenyl-2-yl)-4-(difluoromethyl)-2-methyl-1,3-thiazole-5-carboxamide and acetyl chloride as starting materials, the course of the process (A) according to the invention can be illustrated by the equation below:

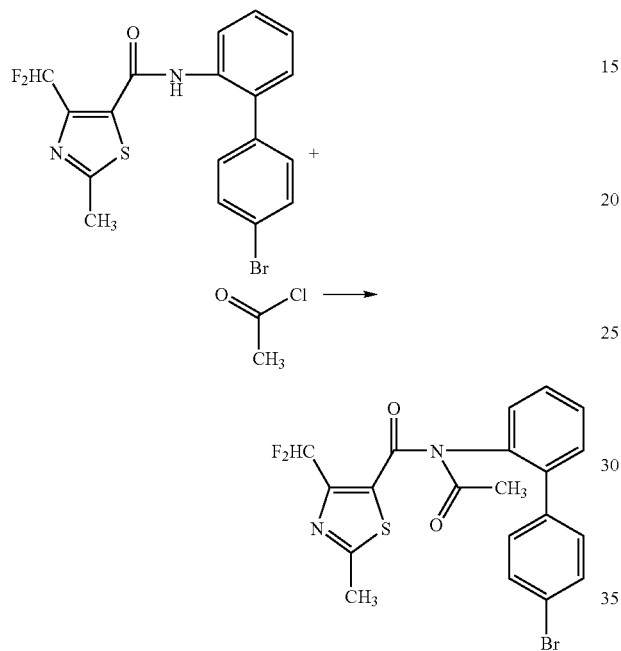

The formula (II) provides a general definition of the thiazolylbiphenylamides required as starting materials for carrying out the process (A) according to the invention. In this formula, $R^1$, $R^2$, $R^3$, $R^4$ and $R^5$ preferably, particularly preferably and very particularly preferably have those meanings which have already been given in connection with the description of the compounds of the formula (I) according to the invention as being preferred, particularly preferred and very particularly preferred, respectively, for these radicals.

Thiazolylbiphenylamides of the formula (II) are described in DE-A 102 04 391. They can be prepared by a) reacting difluoromethylthiazolylcarbonyl halides of the formula (IV)

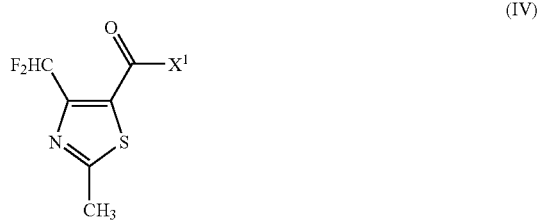

(IV)

in which $X^1$ represents halogen with aniline derivatives of the formula (V)

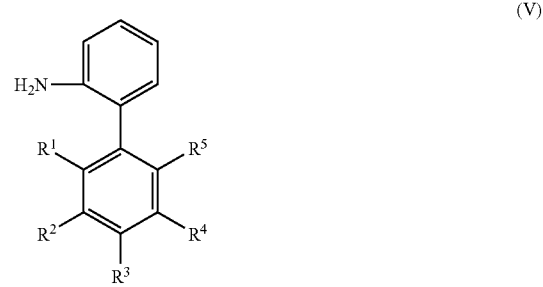

(V)

in which $R^1$, $R^2$, $R^3$, $R^4$ and $R^5$ are as defined above, if appropriate in the presence of an acid binder (for example triethylamine) and if appropriate in the presence of a diluent (for example tetrahydrofuran), or b) reacting difluoromethylthiazolylcarboxhaloanilides of the formula (VI)

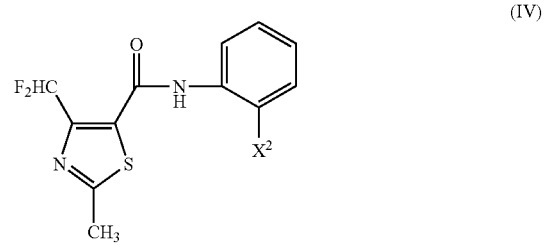

(IV)

in which $X^2$ represents bromine or iodine, with boronic acid derivatives of the formula (VII)

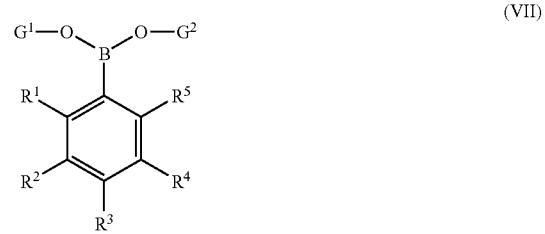

(VII)

in which $R^1$, $R^2$, $R^3$, $R^4$ and $R^5$ are as defined above, $G^1$ and $G^2$ each represent hydrogen or together represent tetramethylethylene, in the presence of a catalyst (for example 1,1'-bis(diphenylphosphino)ferrocenepalladium(II) chloride), if appropriate in the presence of an acid binder (for example potassium acetate) and if appropriate in the presence of a diluent (for example dimethyl sulfoxide), or c) reacting thiazolylbiphenylamide boronic acid derivatives of the formula (VIII)

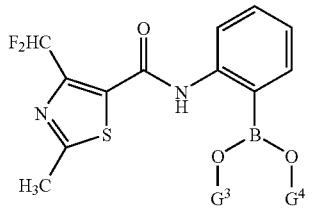

(VIII)

in which
G³ and G⁴ each represent hydrogen or together represent tetramethylethylene,
with halobenzene derivatives of the formula (IX)

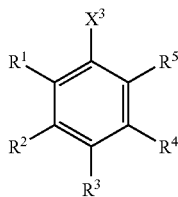

(IX)

in which
$R^1$, $R^2$, $R^3$, $R^4$ and $R^5$ are as defined above,
$X^3$ represents bromine, iodine or trifluoromethylsulfonyloxy,
in the presence of a catalyst (for example 1,1'-bis(diphenylphosphino)ferrocenepalladium(II) chloride), if appropriate in the presence of an acid binder (for example potassium acetate) and if appropriate in the presence of a diluent (for example dimethyl sulfoxide).

The formula (IV) provides a general definition of the difluoromethylthiazolylcarbonyl halides required as starting materials for carrying out the process a) according to the invention. In this formula (IV), $X^1$ preferably represents chlorine. The difluoromethylthiazolylcarbonyl halides of the formula (IV) are known and/or can be prepared by known processes (compare, for example, EP 0 276 177).

The formula (V) provides a general definition of the anilines furthermore required as starting materials for carrying out the process a) according to the invention. In this formula (V), $R^1$, $R^2$, $R^3$, $R^4$ and $R^5$ preferably, particularly preferably and very particularly preferably have those meanings which have already been given in connection with the description of the compounds of the formula (I) according to the invention as being preferred, particularly preferred and very particularly preferred, respectively, for these radicals.

The aniline derivatives of the formula (V) are known and/or can be prepared by known methods (cf., for example, Bull. Korean Chem. Soc. 2000, 21, 165-166; Chem. Pharm. Bull. 1992, 40, 240-4; JP 09132567).

The formula (VI) provides a general definition of the difluoromethylthiazolylcarboxhaloanilides required as starting materials for carrying out the process b) according to the invention. In this formula (VI), $X^2$ preferably represents bromine or iodine.

The difluoromethylthiazolylcarboxhaloanilides of the formula (VI) can be prepared by
d) reacting difluoromethylthiazolylcarbonyl halides of the formula (IV)

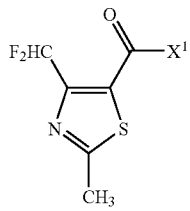

(IV)

in which
$X^1$ represents halogen
with 2-bromoaniline or 2-iodoaniline.

The difluoromethylthiazolylcarbonyl halides of the formula (IV) required as starting materials for carrying out the process d) according to the invention have already been described further above, in connection with the process a) according to the invention.

The compounds 2-bromoaniline or 2-iodoaniline furthermore required as starting materials for carrying out the process d) according to the invention are known chemicals for synthesis.

The formula (VII) provides a general definition of the boronic acid derivatives furthermore required as starting materials for carrying out the process b) according to the invention. In this formula (VII), $R^1$, $R^2$, $R^3$, $R^4$ and $R^5$ preferably, particularly preferably and very particularly preferably have those meanings which have already been given in connection with the description of the compounds of the formula (I) according to the invention as being preferred, particularly preferred and very particularly preferred, respectively, for these radicals. $G^1$ and $G^2$ preferably each represent hydrogen or together represent tetramethylethylene.

Boronic acid derivatives of the formula (VII) are known chemicals for synthesis. It is also possible to prepare them immediately prior to the reaction directly from halobenzene derivatives and boronic acid esters and to react them further without work-up (see also the Preparation Examples).

The formula (VIII) provides a general definition of the thiazolylbiphenylamide boronic acid derivatives required as starting materials for carrying out the process c) according to the invention. In this formula (VIII), $G^3$ and $G^4$ preferably each represent hydrogen or together represent tetramethylethylene.

The thiazolylbiphenylamide boronic acid derivatives of the formula (VIII) can be prepared by
e) reacting difluoromethylthiazolylcarbonyl halides of the formula (IV)

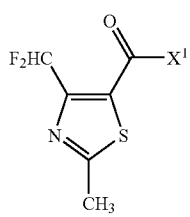

(IV)

in which
X¹ represents halogen
with anilineboronic acid derivatives of the formula (X)

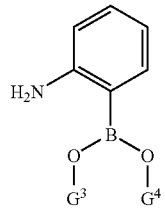

in which
G³ and G⁴ are as defined above,
if appropriate in the presence of an acid binder and if appropriate in the presence of a diluent.

The difluoromethylthiazolylcarbonyl halides of the formula (IV) required as starting materials for carrying out the process e) according to the invention have already been described further above in connection with the process a) according to the invention.

The formula (X) provides a general definition of the anilineboronic acid derivatives furthermore required as starting materials for carrying out the process e) according to the invention. In this formula (X), G³ and G⁴ preferably each represent hydrogen or together represent tetramethylethylene.

The anilineboronic acid derivatives of the formula (X) required as starting materials for carrying out the process e) according to the invention are known chemicals for synthesis.

The formula (IX) provides a general definition of the halobenzene derivatives furthermore required as starting materials for carrying out the process c) according to the invention. In this formula (IX), $R^1$, $R^2$, $R^3$, $R^4$ and $R^5$ preferably, particularly preferably and very particularly preferably have those meanings which have already been given in connection with the description of the compounds of the formula (I) according to the invention as being preferred, particularly preferred and very particularly preferred, respectively, for these radicals. $X^3$ preferably represent bromine, iodine or trifluoromethylsulfonyloxy.

The formula (III) provides a general definition of the halides furthermore required as starting materials for carrying out the process (A) according to the invention. In this formula, $R^6$ preferably, particularly preferably and very particularly preferably has those meanings which have already been given in connection with the description of the compounds of the formula (I) according to the invention as being preferred, particularly preferred and very particularly preferred, respectively, for these radicals. X preferably represents chlorine or bromine.

Halides of the formula (III) are known chemicals for synthesis.

Suitable diluents for carrying out the process (A) according to the invention are all inert organic solvents. These preferably include aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, dichloromethane, chloroform, carbon tetrachloride, dichloroethane or trichloroethane; ethers, such as diethyl ether, diisopropyl ether, methyl tert-butyl ether, methyl tert-amyl ether, dioxane, tetrahydrofuran, 1,2-dimethoxyethane, 1,2-diethoxyethane or anisole or amides, such as N,N-dimethylformamide, N,N-dimethylacetamide, N-methylformanilide, N-methylpyrrolidone or hexamethylphosphoric triamide.

The process (A) according to the invention is, if appropriate, carried out in the presence of a suitable acid acceptor. Suitable acid acceptors are all customary inorganic or organic bases. These preferably include alkaline earth metal or alkali metal hydrides, hydroxides, amides, alkoxides, acetates, carbonates or bicarbonates, such as, for example, sodium hydride, sodium amide, sodium methoxide, sodium ethoxide, potassium tert-butoxide, sodium hydroxide, potassium hydroxide, ammonium hydroxide, sodium acetate, potassium acetate, calcium acetate, ammonium acetate, sodium carbonate, potassium carbonate, potassium bicarbonate, sodium bicarbonate or cesium carbonate, and also tertiary amines, such as trimethylamine, triethylamine, tributylamine, N,N-dimethylaniline, N,N-dimethylbenzylamine, pyridine, N-methylpiperidine, N-methylmorpholine, N,N-dimethylaminopyridine, diazabicyclooctane (DABCO), diazabicyclononene (DBN) or diazabicycloundecene (DBU).

When carrying out the process (A) according to the invention, the reaction temperatures can be varied within a relatively wide range. In general, the process is carried out at temperatures of from 0° C. to 150° C., preferably at temperatures of from 20° C. to 110° C.

For carrying out the process (A) according to the invention for preparing the compounds of the formula (I), in general from 0.2 to 5 mol, preferably from 0.5 to 2 mol, of halide of the formula (III) are employed per mole of the thiazolylbiphenylamide of the formula (II).

Suitable diluents for carrying out the processes a), d) and e) according to the invention are all inert organic solvents. These preferably include aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, dichloromethane, chloroform, carbon tetrachloride, dichloroethane or trichloroethane; ethers, such as diethyl ether, diisopropyl ether, methyl tert-butyl ether, methyl tert-amyl ether, dioxane, tetrahydrofuran, 1,2-dimethoxyethane, 1,2-diethoxyethane or anisole or amides, such as N,N-dimethylformamide, N,N-dimethylacetamide, N-methylformanilide, N-methylpyrrolidone or hexamethylphosphoric triamide.

The processes a), d) and e) according to the invention are, if appropriate, carried out in the presence of a suitable acid acceptor. Suitable acid acceptors are all customary inorganic or organic bases. These preferably include alkaline earth metal or alkali metal hydrides, hydroxides, amides, alkoxides, acetates, carbonates or bicarbonates, such as, for example, sodium hydride, sodium amide, sodium methoxide, sodium ethoxide, potassium tert-butoxide, sodium hydroxide, potassium hydroxide, ammonium hydroxide, sodium acetate, potassium acetate, calcium acetate, ammonium acetate, sodium carbonate, potassium carbonate, potassium bicarbonate, sodium bicarbonate or cesium carbonate, and also tertiary amines, such as trimethylamine, triethylamine, tributylamine, N,N-dimethylaniline, N,N-dimethylbenzylamine, pyridine, N-methylpiperidine, N-methylmorpholine, N,N-dimethylaminopyridine, diazabicyclooctane (DABCO), diazabicyclononene (DBN) or diazabicycloundecene (DBU).

When carrying out the processes a), d) and e) according to the invention, the reaction temperatures can be varied within a relatively wide range. In general, the processes are carried out at temperatures of from 0° C. to 150° C., preferably at temperatures of from 20° C. to 110° C.

For carrying out the process a) according to the invention for preparing the compounds of the formula (II), in general from 0.2 to 5 mol, preferably from 0.5 to 2 mol, of the aniline derivative of the formula (V) are employed per mole of the difluoromethylthiazolylcarbonyl halide of the formula (IV).

For carrying out the process d) according to the invention for preparing the compounds of the formula (V), in general from 0.2 to 5 mol, preferably from 0.5 to 2 mol, of 2-bromoaniline or 2-iodoaniline are employed per mole of the difluoromethylthiazolylcarbonyl halide of the formula (IV).

For carrying out the process e) according to the invention for preparing the compounds of the formula (VIII), in general from 0.2 to 5 mol, preferably from 0.5 to 2 mol, of anilineboronic acid derivative of the formula (X) are employed per mole of the difluoromethylthiazolylcarbonyl halide of the formula (IV).

Suitable diluents for carrying out the processes b) and c) according to the invention are all inert organic solvents. These preferably include aliphatic, alicyclic or aromatic hydrocarbons, such as, for example, petroleum ether, hexane, heptane, cyclohexane, methylcyclohexane, benzene, toluene, xylene or decalin; ethers, such as diethyl ether, diisopropyl ether, methyl tert -butyl ether, methyl tert-amyl ether, dioxane, tetrahydrofuran, 1,2-dimethoxyethane, 1,2-diethoxyethane or anisole; nitriles, such as acetonitrile, propionitrile, n- or isobutyronitrile or benzonitrile; amides, such as N,N-dimethylformamide, N,N-dimethylacetamide, N-methylformanilide, N-methylpyrrolidone or hexamethylphosphoric triamide; esters, such as methyl acetate or ethyl acetate; sulfoxides, such as dimethyl sulfoxide; sulfones, such as sulfolane; alcohols, such as methanol, ethanol, n- or isopropanol, n-, iso-, sec- or tert-butanol, ethanediol, propane-1,2-diol, ethoxyethanol, methoxyethanol, diethylene glycol monomethyl ether, diethylene glycol monoethyl ether, mixtures thereof with water or pure water.

When carrying out the process b) and c) according to the invention, the reaction temperatures can be varied within a relatively wide range. In general, the processes are carried out at temperatures of from 0° C. to 150° C., preferably at temperatures of from 20° C. to 110° C.

The processes b) and c) according to the invention are, if appropriate, carried out in the presence of a suitable acid acceptor. Suitable acid acceptors are all customary inorganic or organic bases. These preferably include alkaline earth metal or alkali metal hydrides, hydroxides, amides, alkoxides, acetates, fluorides, phosphates, carbonates or bicarbonates, such as, for example, sodium hydride, sodium amide, lithium diisopropylamide, sodium methoxide, sodium ethoxide, potassium tertbutoxide, sodium hydroxide, potassium hydroxide, sodium acetate, sodium phosphate, potassium phosphate, potassium fluoride, cesium fluoride, sodium carbonate, potassium carbonate, potassium bicarbonate, sodium bicarbonate or cesium carbonate, and also tertiary amines, such as trimethylamine, triethylamine, tributylamine, N,N-dimethylaniline, N,N-dimethylbenzylamine, pyridine, N-methylpiperidine, N-methylmorpholine, N,N-dimethylaminopyridine, diazabicyclooctane (DABCO), diazabicyclononene (DBN) or diazabicycloundecene (DBU).

The processes b) and c) according to the invention are carried out in the presence of a catalyst, such as, for example, a palladium salt or complex. These are preferably palladium chloride, palladium acetate, tetrakis(triphenylphosphine)palladium, bis(triphenylphosphine)palladium dichloride or (1,1'-bis(diphenylphosphino)-ferrocenepalladium(II) chloride).

It is also possible to generate a palladium complex in the reaction mixture by adding, separately, a palladium salt and a complex ligand, such as, for example, triethylphosphine, tri-tert-butylphosphine, tricyclohexylphosphine, 2-(dicyclohexylphosphine)biphenyl, 2-(di-tert-butylphosphine)biphenyl, 2-(dicyclohexylphosphine)-2'-(N,N-dimethylamino)biphenyl, triphenylphosphine, tris-(o-tolyl)phosphine, sodium 3-(diphenylphosphino)benzenesulfonate, tris-2-(methoxyphenyl)phosphine, 2,2'-bis(diphenylphosphine)-1,1'-binaphthyl, 1,4-bis-(diphenylphosphine)butane, 1,2-bis(diphenylphosphine)ethane, 1,4-bis(dicyclohexylphosphine)butane, 1,2-bis(dicyclohexylphosphine)ethane, 2-(dicyclohexylphosphine)-2'-(N,N-dimethylamino)biphenyl, bis(diphenylphosphino)ferrocene or tris-(2,4-tert-butylphenyl)phosphite to the reaction.

For carrying out the process b) for preparing the compounds of the formula (II), in general from 1 to 15 mol, preferably from 2 to 8 mol, of boronic acid derivative of the formula (VII) are employed per mole of the difluoromethylthiazolylcarboxhaloanilide of the formula (VI).

For carrying out process c) according to the invention for preparing the compounds of the formula (II), in general from 1 to 15 mol, preferably from 2 to 8 mol, of halobenzene derivative of the formula (IX) are employed per mole of the thiazolylbiphenylamide boronic acid derivative of the formula (VIII).

The processes (A), a), b), c) and d) according to the invention are generally carried out under atmospheric pressure. However, it is also possible to operate under elevated or reduced pressure—in general between 0.1 bar and 10 bar.

The compounds according to the invention have potent microbicidal activity and can be employed for controlling unwanted microorganisms, such as fungi and bacteria, in crop protection and in the protection of materials.

Fungicides can be employed in crop protection for controlling Plasmodiophoromycetes, Oomycetes, Chytridiomycetes, Zygomycetes, Ascomycetes, Basidiomycetes and Deuteromycetes.

Bactericides can be employed in crop protection for controlling Pseudomonadaceae, Rhizobiaceae, Enterobacteriaceae, Corynebacteriaceae and Streptomycetaceae.

Some pathogens causing fungal and bacterial diseases which come under the generic names listed above may be mentioned as examples, but not by way of limitation:

*Xanthomonas* species, such as, for example, *Xanthomonas campestris* pv. *oryzae;*

*Pseudomonas* species, such as, for example, *Pseudomonas syringae* pv. *lachrymans;*

*Erwinia* species, such as, for example, *Erwinia amylovora;*

*Pythium* species, such as, for example, *Pythium ultimum;*

*Phytophthora* species, such as, for example, *Phytophthora infestans;*

*Pseudoperonospora* species, such as, for example, *Pseudoperonospora humuli* or *Pseudoperonospora cubensis;*

*Plasmopara* species, such as, for example, *Plasmopara viticola;*

*Bremia* species, such as, for example, *Bremia lactucae;*

*Peronospora* species, such as, for example, *Peronospora pisi* or *P. brassicae;*

*Erysiphe* species, such as, for example, *Erysiphe graminis;*

*Sphaerotheca* species, such as, for example, *Sphaerotheca fuliginea;*

*Podosphaera* species, such as, for example, *Podosphaera leucotricha;*

*Venturia* species, such as, for example, *Venturia inaequalis;*

*Pyrenophora* species, such as, for example, *Pyrenophora teres* or *P. graminea* (conidia form: *Drechslera*, syn: *Helminthosporium*);

*Cochliobolus* species, such as, for example, *Cochliobolus sativus* (conidia form: *Drechslera*, syn: *Helminthosporium*);

*Uromyces* species, such as, for example, *Uromyces appendiculatus*;

*Puccinia* species, such as, for example, *Puccinia recondita*;

*Sclerotinia* species, such as, for example, *Sclerotinia sclerotiorum*;

*Tilletia* species, such as, for example, *Tilletia caries*;

*Ustilago* species, such as, for example, *Ustilago nuda* or *Ustilago avenae*;

*Pellicularia* species, such as, for example, *Pellicularia sasakii*;

*Pyricularia* species, such as, for example, *Pyricularia oryzae*;

*Fusarium* species, such as, for example, *Fusarium culmorum*;

*Botrytis* species, such as, for example, *Botrytis cinerea*;

*Septoria* species, such as, for example, *Septoria nodorum*;

*Leptosphaeria* species, such as, for example, *Leptosphaeria nodorum*;

*Cercospora* species, such as, for example, *Cercospora canescens*;

*Alternaria* species, such as, for example, *Alternaria brassicae*; and

*Pseudocercosporella* species, such as, for example, *Pseudocercosporella herpotrichoides*.

The active compounds according to the invention also show a strong invigorating action in plants. Accordingly, they are suitable for mobilizing the internal defenses of the plant against attack by unwanted microorganisms.

In the present context, plant-invigorating (resistance-inducing) compounds are to be understood as meaning substances which are capable of stimulating the defense system of plants such that, when the treated plants are subsequently inoculated with unwanted microorganisms, they display substantial resistance to these microorganisms.

In the present case, unwanted microorganisms are to be understood as meaning phytopathogenic fungi, bacteria and viruses. The compounds according to the invention can thus be used to protect plants within a certain period of time after treatment against attack by the pathogens mentioned. The period of time for which this protection is achieved generally extends for 1 to 10 days, preferably 1 to 7 days, from the treatment of the plants with the active compounds.

The fact that the active compounds are well tolerated by plants at the concentrations required for controlling plant diseases permits the treatment of above-ground parts of plants, of propagation stock and seeds, and of the soil.

The active compounds according to the invention can be used with particularly good results for controlling diseases in viticulture and in the cultivation of fruits and vegetables, such as, for example, against *Venturia*, *Botrytis*, *Sclerotinia*, *Rhizoctonia*, *Uncinula*, *Sphaerotheca*-, *Podosphaera*, *Alternaria* and *Colletotrichum* species. Rice diseases, such as *Pyricularia* and *Pellicularia* species, are likewise controlled with good results.

The active compounds according to the invention are also suitable for increasing the yield of crops. In addition, they show reduced toxicity and are well tolerated by plants.

If appropriate, the active compounds according to the invention can, at certain concentrations and application rates, also be employed as herbicides, for regulating plant growth and for controlling animal pests. If appropriate, they can also be used as intermediates or precursors in the synthesis of other active compounds.

According to the invention, it is possible to treat all plants and parts of plants. Plants are to be understood here as meaning all plants and plant populations, such as desired and undesired wild plants or crop plants (including naturally occurring crop plants). Crop plants can be plants which can be obtained by conventional breeding and optimization methods or by biotechnological and genetic engineering methods or combinations of these methods, including the transgenic plants and including plant cultivars which can or cannot be protected by plant breeders' certificates. Parts of plants are to be understood as meaning all above-ground and below-ground parts and organs of plants, such as shoot, leaf, flower and root, examples which may be mentioned being leaves, needles, stems, trunks, flowers, fruit-bodies, fruits and seeds and also roots, tubers and rhizomes. Parts of plants also include harvested material and vegetative and generative propagation material, for example seedlings, tubers, rhizomes, cuttings and seeds.

The treatment of the plants and parts of plants according to the invention with the active compounds is carried out directly or by action on their environment, habitat or storage area according to customary treatment methods, for example by dipping, spraying, evaporating, atomizing, broadcasting, brushing-on, injecting and, in the case of propagation material, in particular in the case of seeds, furthermore by one- or multilayer coating.

In the protection of materials, the compounds according to the invention can be employed for protecting industrial materials against infection with, and destruction by, unwanted microorganisms.

Industrial materials in the present context are understood as meaning non-living materials which have been prepared for use in industry. For example, industrial materials which are intended to be protected by active compounds according to the invention from microbial change or destruction can be tackifiers, sizes, paper and board, textiles, leather, wood, paints and plastic articles, cooling lubricants and other materials which can be infected with, or destroyed by, microorganisms. Parts of production plants, for example cooling-water circuits, which may be impaired by the proliferation of microorganisms may also be mentioned within the scope of the materials to be protected. Industrial materials which may be mentioned within the scope of the present invention are preferably tackifiers, sizes, paper and board, leather, wood, paints, cooling lubricants and heat-transfer liquids, particularly preferably wood.

Microorganisms capable of degrading or changing the industrial materials which may be mentioned are, for example, bacteria, fungi, yeasts, algae and slime organisms. The active compounds according to the invention preferably act against fungi, in particular molds, wood-discoloring and wood-destroying fungi (Basidiomycetes) and against slime organisms and algae.

Microorganisms of the following genera may be mentioned as examples:

*Alternaria*, such as *Alternaria tenuis*,

*Aspergillus*, such as *Aspergillus niger*,

*Chaetomium*, such as *Chaetomium globosum*,

*Coniophora*, such as *Coniophora puetana*,

*Lentinus*, such as *Lentinus tigrinus*,

*Penicillium*, such as *Penicillium glaucum*,

*Polyporus*, such as *Polyporus versicolor*,

*Aureobasidium*, such as *Aureobasidium pullulans*,

*Sclerophoma*, such as *Sclerophoma pityophila*,

*Trichoderma*, such as *Trichoderma viride*,

*Escherichia*, such as *Escherichia coli*,

*Pseudomonas*, such as *Pseudomonas aeruginosa*, and

*Staphylococcus*, such as *Staphylococcus aureus*.

Depending on their particular physical and/or chemical properties, the active compounds can be converted into the customary formulations, such as solutions, emulsions, suspensions, powders, foams, pastes, granules, aerosols and microencapsulations in polymeric substances and in coating compositions for seeds, and ULV cool and warm fogging formulations.

These formulations are produced in a known manner, for example by mixing the active compounds with extenders, that is liquid solvents, liquefied gases under pressure, and/or solid carriers, optionally with the use of surfactants, that is emulsifiers and/or dispersants, and/or foam formers. If the extender used is water, it is also possible to employ, for example, organic solvents as auxiliary solvents. Essentially, suitable liquid solvents are: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide or dimethyl sulfoxide, or else water. Liquefied gaseous extenders or carriers are to be understood as meaning liquids which are gaseous at standard temperature and under atmospheric pressure, for example aerosol propellants such as halogenated hydrocarbons, or else butane, propane, nitrogen and carbon dioxide. Suitable solid carriers are: for example ground natural minerals such as kaolins, clays, talc, chalk, quartz, attapulgite, montmorillonite or diatomaceous earth, and ground synthetic minerals such as finely divided silica, alumina and silicates. Suitable solid carriers for granules are: for example crushed and fractionated natural rocks such as calcite, pumice, marble, sepiolite and dolomite, or else synthetic granules of inorganic and organic meals, and granules of organic material such as sawdust, coconut shells, maize cobs and tobacco stalks. Suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulfonates, alkyl sulfates, arylsulfonates, or else protein hydrolysates. Suitable dispersants are: for example lignosulfite waste liquors and methylcellulose.

Tackifiers such as carboxymethylcellulose, natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other possible additives are mineral and vegetable oils.

It is possible to use colorants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 percent by weight of active compound, preferably between 0.5 and 90%.

The active compounds according to the invention can, as such or in their formulations, also be used in a mixture with known fungicides, bactericides, acaricides, nematicides or insecticides, to broaden, for example, the activity spectrum or to prevent development of resistance. In many cases, synergistic effects are obtained, i.e. the activity of the mixture is greater than the activity of the individual components.

Suitable mixing components are, for example, the following compounds:

Fungicides:

2-phenylphenol; 8-hydroxyquinoline sulfate; acibenzolar-5-methyl; aldimorph; amidoflumet; ampropylfos; ampropylfos-potassium; andoprim; anilazine; azaconazole; azoxystrobin;

benalaxyl; benodanil; benomyl; benthiavalicarb-isopropyl; benzamacril; benzamacril-isobutyl; bilanafos; binapacryl; biphenyl; bitertanol; blasticidin-S; bromuconazole; bupirimate; buthiobate; butylamine;

calcium polysulfide; capsimycin; captafol; captan; carbendazim; carboxin; carpropamid; carvone; chinomethionat; chlobenthiazone; chlorfenazole; chloroneb; chlorothalonil; chlozolinate; clozylacon; cyazofamid; cyflufenamid; cymoxanil; cyproconazole; cyprodinil; cyprofuram;

Dagger G; debacarb; dichlofluanid; dichlone; dichlorophen; diclocymet; diclomezine; dicloran; diethofencarb; difenoconazole; diflumetorim; dimethirimol; dimethomorph; dimoxystrobin; diniconazole; diniconazole-M; dinocap; diphenylamine; dipyrithione; ditalimfos; dithianon; dodine; drazoxolon;

edifenphos; epoxiconazole; ethaboxam; ethirimol; etridiazole;

famoxadone; fenamidone; fenapanil; fenarimol; fenbuconazole; fenfuram; fenhexamid; fenitropan; fenoxanil; fenpiclonil; fenpropidin; fenpropimorph; ferbam; fluazinam; flubenzimine; fludioxonil; flumetover; flumorph; fluoromide; fluoxastrobin; fluquinconazole; flurprimidol; flusilazole; flusulfamide; flutolanil; flutriafol; folpet; fosetyl-Al; fosetyl-sodium; fuberidazole; furalaxyl; furametpyr; furcarbanil; furmecyclox;

guazatine; hexachlorobenzene; hexaconazole; hymexazole;

imazalil; imibenconazole; iminoctadine triacetate; iminoctadine tris(albesil); iodocarb; ipconazole; iprobenfos; iprodione; iprovalicarb; irumamycin; isoprothiolane; isovaledione;

kasugamycin; kresoxim-methyl;

mancozeb; maneb; meferimzone; mepanipyrim; mepronil; metalaxyl; metalaxyl-M; metconazole; methasulfocarb; methfuroxam; metiram; metominostrobin; metsulfovax; mildiomycin; myclobutanil; myclozolin;

natamycin; nicobifen; nitrothal-isopropyl; noviflumuron; nuarimol;

ofurace; orysastrobin; oxadixyl; oxolinic acid; oxpoconazole; oxycarboxin; oxyfenthiin;

paclobutrazole; pefurazoate; penconazole; pencycuron; phosdiphen; phthalide; picoxystrobin; piperalin; polyoxins; polyoxorim; probenazole; prochloraz; procymidone; propamocarb; propanosine-sodium; propiconazole; propineb; proquinazid; prothioconazole; pyraclostrobin; pyrazophos; pyrifenox; pyrimethanil; pyroquilon; pyroxyfur; pyrrolenitrine;

quinconazole; quinoxyfen; quintozene; simeconazole; spiroxamine; sulfur;

tebuconazole; tecloftalam; tecnazene; tetcyclacis; tetraconazole; thiabendazole; thicyofen; thifluzamide; thiophanate-methyl; thiram; tioxymid; tolclofos-methyl; tolylfluanid; triadimefon; triadimenol; triazbutil; triazoxide; tricyclamide; tricyclazole; tridemorph; trifloxystrobin; triflumizole; triforine; triticonazole;

uniconazole; validamycin A; vinclozolin; zineb; ziram; zoxamide;

(2S)-N-[2-[4-[[3-(4-chlorophenyl)-2-propynyl]oxy]-3-methoxyphenyl]ethyl]-3-methyl-2-[(methylsulfonyl)amino] butanamide; 1-(1-naphthalenyl)-1H-pyrrole-2,5-dione; 2,3,5,6-tetrachloro-4-(methylsulfonyl)pyridine; 2-amino-4-methyl-N-phenyl-5-thiazolecarboxamide; 2-chloro-N-(2,3-dihydro-1,1,3-trimethyl-1H-inden-4-yl)-3-pyridinecarboxamide; 3,4,5-trichloro-2,6-pyridinedicarbonitrile; actinovate; cis-1-(4-chlorophenyl)-2-

(1H-1,2,4-triazol-1-yl)cycloheptanol; methyl 1-(2,3-dihydro-2,2-dimethyl-1H-inden-1-yl)-1H-imidazole-5-carboxylate; monopotassium carbonate; N-(6-methoxy-3-pyridinyl)-cyclopropanecarboxamide; N-butyl-8-(1,1-dimethylethyl)-1-oxaspiro[4.5]decane-3-amine; sodium tetrathiocarbonate;

and copper salts and preparations, such as Bordeaux mixture; copper hydroxide; copper naphthenate; copper oxychloride; copper sulfate; cufraneb; copper oxide; mancopper; oxine-copper.

Bactericides:

bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulfate and other copper preparations.

Insecticides/acaricides/nematicides:

abamectin, ABG-9008, acephate, acequinocyl, acetamiprid, acetoprole, acrinathrin, AKD-1022, AKD-3059, AKD-3088, alanycarb, aldicarb, aldoxycarb, allethrin, allethrin 1R-isomers, alpha-cypermethrin (alphamethrin), amidoflumet, aminocarb, amitraz, avermectin, AZ-60541, azadirachtin, azamethiphos, azinphos-methyl, azinphos-ethyl, azocyclotin,

*Bacillus popilliae, Bacillus sphaericus, Bacillus subtilis, Bacillus thuringiensis, Bacillus thuringiensis* strain EG-2348, *Bacillus thuringiensis* strain GC-91, *Bacillus thuringiensis* strain NCTC-11821, baculoviruses, *Beauveria bassiana, Beauveria tenella*, benclothiaz, bendiocarb, benfuracarb, bensultap, benzoximate, beta-cyfluthrin, beta-cypermethrin, bifenazate, bifenthrin, binapacryl, bioallethrin, bioallethrinS-cyclopentyl-isomer, bioethanomethrin, biopermethrin, bioresmethrin, bistrifluoron, BPMC, brofenprox, bromophos-ethyl, bromopropylate, bromfenvinfos (-methyl), BTG-504, BTG-505, bufencarb, buprofezin, butathiofos, butocarboxim, butoxycarboxim, butylpyridaben, cadusafos, camphechlor, carbaryl, carbofuran, carbophenothion, carbosulfan, cartap, CGA-50439, quinomethionate, chlordane, chlordimeform, chloethocarb, chlorethoxyfos, chlorfenapyr, chlorfenvinphos, chlorfluazuron, chlormephos, chlorobenzilate, chloropicrin, chlorproxyfen, chlorpyrifos-methyl, chlorpyrifos (-ethyl), chlovaporthrin, chromafenozide, cis-cypermethrin, cis-resmethrin, cis-permethrin, clocythrin, cloethocarb, clofentezine, clothianidin, clothiazoben, codlemone, coumaphos, cyanofenphos, cyanophos, cycloprene, cycloprothrin, *Cydia pomonella*, cyfluthrin, cyhalothrin, cyhexatin, cypermethrin, cyphenothrin (1R-trans-isomer), cyromazine, DDT, deltamethrin, demeton-5-methyl, demeton-5-methylsulfone, diafenthiuron, dialifos, diazinon, dichlofenthion, dichlorvos, dicofol, dicrotophos, dicyclanil, diflubenzuron, dimefluthrin, dimethoate, dimethylvinphos, dinobuton, dinocap, dinotefuran, diofenolan, disulfoton, docusat-sodium, dofenapyn, DOWCO-439, eflusilanate, emamectin, emamectin-benzoate, empenthrin (1R-isomer), endosulfan, *Entomopthora* spp., EPN, esfenvalerate, ethiofencarb, ethiprole, ethion, ethoprophos, etofenprox, etoxazole, etrimfos, famphur, fenamiphos, fenazaquin, fenbutatin oxide, fenfluthrin, fenitrothion, fenobucarb, fenothiocarb, fenoxacrim, fenoxycarb, fenpropathrin, fenpyrad, fenpyrithrin, fenpyroximate, fensulfothion, fenthion, fentrifanil, fenvalerate, fipronil, flonicamid, fluacrypyrim, fluazuron, flubenzimine, flubrocythrinate, flucycloxuron, flucythrinate, flufenerim, flufenoxuron, flufenprox, flumethrin, flupyrazofos, flutenzin (flufenzine), fluvalinate, fonofos, formetanate, formothion, fosmethilan, fosthiazate, fubfenprox (fluproxyfen), furathiocarb, gamma-HCH, gossyplure, grandlure, granulosis viruses, halfenprox, halofenozide, HCH, HCN-801, heptenophos, hexaflumuron, hexythiazox, hydramethylnone, hyprodene, IKA-2002, imidacloprid, imiprothrin, indoxacarb, iodofenphos, iprobenfos, isazofos, isofenphos, isoprocarb, isoxathion, ivermectin, japonilure, kadethrin, nuclear polyhedrosis viruses, kinoprene, lambda-cyhalothrin, lindane, lufenuron, malathion, mecarbam, mesulfenfos, metaldehyde, metam-sodium, methacrifos, methamidophos, *Metharhizium anisopliae, Metharhizium flavoviride*, methidathion, methiocarb, methomyl, methoprene, methoxychlor, methoxyfenozide, metofluthrin, metolcarb, metoxadiazone, mevinphos, milbemectin, milbemycin, MKI-245, MON-45700, monocrotophos, moxidectin, MTI-800, naled, NC-104, NC-170, NC-184, NC-194, NC-196, niclosamide, nicotine, nitenpyram, nithiazine, NNI-0001, NNI-0101, NNI-0250, NNI-9768, novaluron, noviflumuron, OK-5101, OK-5201, OK-9601, OK-9602, OK-9701, OK-9802, omethoate, oxamyl, oxydemeton-methyl,

*Paecilomyces fumosoroseus*, parathion-methyl, parathion (-ethyl), permethrin (cis-, trans-), petroleum, PH-6045, phenothrin (1R-trans isomer), phenthoate, phorate, phosalone, phosmet, phosphamidon, phosphocarb, phoxim, piperonyl butoxide, pirimicarb, pirimiphos-methyl, pirimiphos-ethyl, potassium oleate, prallethrin, profenofos, profluthrin, promecarb, propaphos, propargite, propetamphos, propoxur, prothiofos, prothoate, protrifenbute, pymetrozine, pyraclofos, pyresmethrin, pyrethrum, pyridaben, pyridalyl, pyridaphenthion, pyridathion, pyrimidifen, pyriproxyfen, quinalphos, resmethrin, RH-5849, ribavirin, RU-12457, RU-15525, S-421, S-1833, salithion, sebufos, SI-0009, silafluofen, spinosad, spirodiclofen, spiromesifen, sulfluramid, sulfotep, sulprofos, SZI-121, tau-fluvalinate, tebufenozide, tebufenpyrad, tebupirimfos, teflubenzuron, tefluthrin, temephos, temivinphos, terbam, terbufos, tetrachlorvinphos, tetradifon, tetramethrin, tetramethrin (1R-isomer), tetrasul, theta-cypermethrin, thiacloprid, thiamethoxam, thiapronil, thiatriphos, thiocyclam hydrogenoxalate, thiodicarb, thiofanox, thiometon, thiosultap-sodium, thuringiensin, tolfenpyrad, tralocythrin, tralomethrin, transfluthrin, triarathene, triazamate, triazophos, triazuron, trichlophenidine, trichlorfon, triflumuron, trimethacarb, vamidothion, vaniliprole, verbutin, *Verticillium lecanii*, WL-108477, WL-40027, yl-5201, yl-5301, yl-5302, XMC, xylylcarb, ZA-3274, zeta-cypermethrin, zolaprofos, ZXI-8901, the compound 3-methylphenyl propylcarbamate (Tsumacide Z), the compound 3-(5-chloro-3-pyridinyl)-8-(2,2,2-trifluoroethyl)-8-azabicyclo[3.2.1]octane-3-carbonitrile (CAS-Reg. No. 185982-80-3) and the corresponding 3-endo-isomer (CAS-Reg. No. 185984-60-5) (cf. WO-96/37494, WO-98/25923), and preparations which comprise insecticidally active plant extracts, nematodes, fungi or viruses.

A mixture with other known active compounds, such as herbicides, or with fertilizers and growth regulators, safeners and/or semicochemicals is also possible.

In addition, the compounds of the formula (I) according to the invention also have very good antimycotic activity. They have a very broad antimycotic activity spectrum in particular against dermatophytes and yeasts, molds and diphasic fungi (for example against *Candida* species such as *Candida albicans, Candida glabrata*) and *Epidermophyton floccosum, Aspergillus* species such as *Aspergillus niger* and *Aspergillus fumigatus, Trichophyton* species such as *Trichophyton mentagrophytes, Microsporon* species such as *Microsporon canis* and *audouinii*. The list of these fungi does by no means limit the mycotic spectrum which can be covered, but is only for illustration.

The active compounds can be used as such, in the form of their formulations or the use forms prepared therefrom, such as ready-to-use solutions, suspensions, wettable powders, pastes, soluble powders, dusts and granules. Application is carried out in a customary manner, for example by watering, spraying, atomizing, broadcasting, dusting, foaming, spreading, etc. It is furthermore possible to apply the active compounds by the ultra-low volume method, or to inject the active compound preparation or the active compound itself into the soil. It is also possible to treat the seeds of the plants.

When using the active compounds according to the invention as fungicides, the application rates can be varied within a relatively wide range, depending on the kind of application. For the treatment of parts of plants, the active compound application rates are generally between 0.1 and 10 000 g/ha, preferably between 10 and 1000 g/ha. For seed dressing, the active compound application rates are generally between 0.001 and 50 g per kilogram of seed, preferably between 0.01 and 10 g per kilogram of seed. For the treatment of the soil, the active compound application rates are generally between 0.1 and 10 000 g/ha, preferably between 1 and 5000 g/ha.

The compositions used for protecting engineered materials generally comprise the active compounds in an amount of from 1 to 95%, preferably from 10 to 75%.

The use concentrations of the active compounds according to the invention depend on the type and the occurrence of the microorganisms to be controlled, and on the composition of the material to be protected. The optimal rate can be determined by test series. In general, the use concentrations are in the range from 0.001 to 5% by weight, preferably from 0.05 to 1.0% by weight, based on the material to be protected.

The activity and the activity spectrum of the active compounds to be used according to the invention in the protection of materials or of the compositions, concentrates or quite generally formulations which can be prepared therefrom can be increased by adding, if appropriate, further antimicrobially active compounds, fungicides, bactericides, herbicides, insecticides or other active compounds to widen the activity spectrum or to obtain particular effects, such as, for example, additional protection against insects. These mixtures may have a wider activity spectrum than the compounds according to the invention.

When used as insecticides, the active compounds according to the invention can furthermore be present in their commercially available formulations and in the use forms, prepared from these formulations, as a mixture with synergists. Synergists are compounds which increase the activity of the active compounds, without it being necessary for the synergist added to be active itself.

When used as insecticides, the active compounds according to the invention can furthermore be present in their commercially available formulations and in the use forms, prepared from these formulations, as a mixture with inhibitors which reduce the degradation of the active compound after use in the vicinity of the plant, on the surface of plant parts or in plant tissues.

The active compound content of the use forms prepared from the commercially available formulations can vary within wide limits. The active compound concentration of the use forms can be from 0.0000001 to 95% by weight of active compound, preferably between 0.0001 and 1% by weight.

They are applied in a customary manner adapted to suit the use forms.

When used against hygiene pests and pests of stored products, the active compound has excellent residual action on wood and clay as well as a good stability to alkali on limed substrates.

As already mentioned above, it is possible to treat all plants and their parts according to the invention. In a preferred embodiment, wild plant species and plant cultivars, or those obtained by conventional biological breeding, such as crossing or protoplast fusion, and parts thereof, are treated. In a further preferred embodiment, transgenic plants and plant cultivars obtained by genetic engineering, if appropriate in combination with conventional methods (Genetically Modified Organisms), and parts thereof, are treated. The term "parts" or "parts of plants" or "plant parts" has been explained above.

Particularly preferably, plants of the plant cultivars which are in each case commercially available or in use are treated according to the invention. Plant cultivars are to be understood as meaning plants having new properties ("traits") and which have been obtained by conventional breeding, by mutagenesis or by recombinant DNA techniques. They can be cultivars, varieties, bio- or genotypes.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions which can be used according to the invention, better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products are possible which exceed the effects which were actually to be expected.

The transgenic plants or plant cultivars (i.e. those obtained by genetic engineering) which are preferably to be treated according to the invention include all plants which, in the genetic modification, received genetic material which imparted particularly advantageous useful properties ("traits") to these plants. Examples of such properties are better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products. Further and particularly emphasized examples of such properties are a better defense of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, cotton, tobacco, oilseed rape and also fruit plants (with the fruits apples, pears, citrus fruits and grapes), and particular emphasis is given to maize, soya beans, potatoes, cotton, tobacco and oilseed rape. Traits that are emphasized are in particular increased defense of the plants against insects, arachnids, nematodes and slugs and snails by toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF and also combinations thereof) (hereinbelow referred to as "Bt plants"). Traits that are also particularly emphasized are the increased defense of the plants against fungi, bacteria and viruses by systemic acquired resistance (SAR), systemin, phytoalexins, elicitors and resistance genes and correspondingly expressed proteins and toxins. Traits that are furthermore particularly emphasized are the increased tolerance of the plants to certain herbicidally active compounds, for example imidazolinones, sulfonylureas, glyphosate or phosphinotricin (for example the "PAT" gene). The genes which impart the desired traits in question can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya beans), Knock-Out® (for example maize), StarLink® (for example maize), Bollgard® (cotton), Nucoton® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinotricin, for example oilseed rape), IMI® (tolerance to imidazolinones) and STS® (tolerance to sulfonylureas, for example maize). Herbicide-resistant plants (plants bred in a conventional manner for herbicide tolerance) which may be mentioned also include the varieties sold under the name Clearfield® (for example maize). Of course, these statements also apply to plant cultivars which have these genetic traits or genetic traits still to be developed, and which will be developed and/or marketed in the future.

The plants listed can be treated according to the invention in a particularly advantageous manner with the compounds of the general formula (I) or the active compound mixtures according to the invention. The preferred ranges stated above for the active compounds or mixtures also apply to the treatment of these plants. Particular emphasis is given to the treatment of plants with the compounds or mixtures specifically mentioned in the present text.

The preparation and the use of the active compounds according to the invention is illustrated by the examples below.

PREPARATION EXAMPLES

Example 1

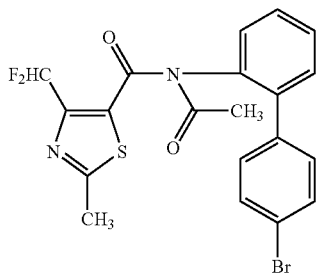

N-(4'-Bromo-1,1'-biphenyl-2-yl)-4-(difluoromethyl)-2-methyl-1,3-thiazole-5-carboxamide (0.3 g, 0.7 mmol) is initially charged in tetrahydrofuran (20 ml), and sodium hydride (60%, 34 mg, 0.85 mmol) is added. After 15 min at room temperature, acetyl chloride (50 μl, 0.7 mmol) is added, and the mixture is stirred at 50° C. for 5 h.

For work-up, the mixture is washed with saturated sodium bicarbonate solution and extracted with ethyl acetate, and the extract is dried with sodium sulfate and concentrated under reduced pressure.

This gives 0.31 g (95% of theory) of N-acetyl-N-(4'-bromo-1,1'-biphenyl-2-yl)-4-(difluoromethyl)-2-methyl-1,3-thiazole-5-carboxamide of log P (pH 2.3)=3.61.

Example 2

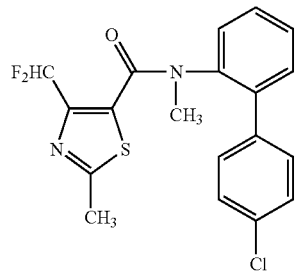

N-(4'-Chloro-1,1'-biphenyl-2-yl)-4-(difluoromethyl)-2-methyl-1,3-thiazole-5-carboxamide (0.3 g, 0.8 mmol) is initially charged in tetrahydrofuran, and sodium hydride (60%, 23 mg, 1.0 mmol) is added. After 15 min at room temperature, methyl iodide (100 μl, 1.6 mmol) is added and the mixture is heated under reflux for 16 h.

For work-up, the mixture is washed with sodium bicarbonate solution and extracted with ethyl acetate, and the organic phase is dried over sodium sulfate, filtered and concentrated.

This gives 0.25 g (80% of theory) of N-(4'-chloro-1,1'-biphenyl-2-yl)-4-difluoromethyl)-N,2-dimethyl-1,3-thiazole-5-carboxamide of log P (pH 2.3)=3.34.

The compounds of the formula (I) listed in table 1 below are obtained analogously to examples 1 and 2 and in accordance with the statements in the general description of the process (A).

TABLE 1

(I)

| Ex. | $R^1$ | $R^2$ | $R^3$ | $R^4$ | $R^5$ | $R^6$ | logP |
|---|---|---|---|---|---|---|---|
| 3 | H | $CH_3$ | Cl | H | H | 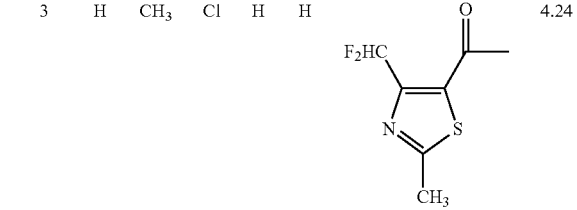 | 4.24 |

TABLE 1-continued

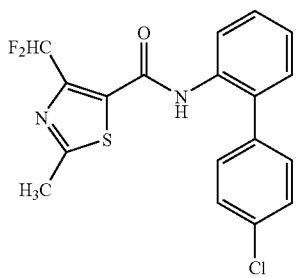

| Ex. | R¹ | R² | R³ | R⁴ | R⁵ | R⁶ | logP |
|---|---|---|---|---|---|---|---|
| 4 | H | Cl | H | Cl | H | ![structure with F₂HC-thiazole-CH₃ acyl] | 4.28 |
| 5 | H | H | Cl | H | H | ![structure with F₂HC-thiazole-CH₃ acyl] | 3.94 |
| 6 | H | H | Br | H | H | —CH₃ | 3.44 |
| 7 | H | H | F | H | H | —CH₃ | 2.99 |
| 8 | H | H | F | H | H | —COCH₃ | 3.16 |
| 9 | H | H | Cl | H | H | —COCH₂OCH₃ | 3.34 |

Preparation of Starting Materials of the Formula (II)

Example (II-1)

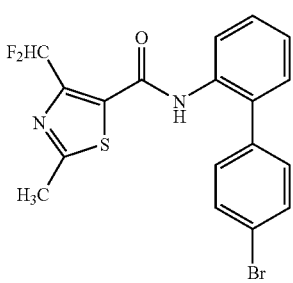

At a temperature between –10 and –20° C., a solution of 21.8 g (0.10 mol) of 2-methyl-4-(difluoromethyl)-1,3-thiazole-5-carbonyl chloride in 200 ml of tetrahydrofuran is added slowly to 23.2 g (0.09 mol) of 4'-bromo-1,1'-biphenyl-2-amine and 26.0 ml (0.19 mol) of triethylamine in 1.0 l of tetrahydrofuran. The reaction solution is stirred at 0° C. for 2 h. For work-up, the mixture is concentrated and chromatographed on silica gel using cyclohexane/ethyl acetate.

This gives 27.8 g (70% of theory) of N-(4'-bromo-1,1'-biphenyl-2-yl)-2-methyl-4-(difluoromethyl)-1,3-thiazole-5-carboxamide of log P (pH 2.3)=3.34 and melting point 151° C.

Example (II-2)

At a temperature between –10° C. and –20° C., a solution of 56.3 g (0.27 mol) of 2-methyl-4-(difluoromethyl)-1,3-thiazole-5-carbonyl chloride in 500 ml of tetrahydrofuran is added slowly to 65.1 g (0.32 mol) of 4'-bromo-1,1'-biphenyl-2-amine and 74.0 ml (0.53 mol) of triethylamine in 2.0 l of tetrahydrofuran. The reaction solution is stirred at 0° C. for 2 h. For work-up, the mixture is concentrated and chromatographed on silica gel using cyclohexane/ethyl acetate.

This gives 43.88 g (44.5% of theory) of N-(4'-chloro-1,1'-biphenyl-2-yl)-2-methyl-4-(difluoromethyl)-1,3-thiazole-5-carboxamide of log P (pH 2.3)=3.26 and melting point 144° C.

The log P values given in the preparation examples and tables above are determined in accordance with EEC Directive 79/831 Annex V.A8 by HPLC (High Performance Liquid Chromatography) using a reversed-phase column (C 18). Temperature: 43° C.

The determination is carried out in the acidic range at pH 2.3 using the mobile phases 0.1% aqueous phosphoric acid and acetonitrile; linear gradient from 10% acetonitrile to 90% acetonitrile.

Calibration is carried out using unbranched alkan-2-ones (having 3 to 16 carbon atoms) with known log P values (determination of the log P values by the retention times using linear interpolation between two successive alkanones).

The lambda max values were determined in the maxima of the chromatographic signals using the UV spectra from 200 nm to 400 nm.

Use Examples

Example A

*Sphaerotheca* Test (Cucumber)/Protective

Solvents: 24.5 parts by weight of acetone
24.5 parts by weight of dimethylacetamide
Emulsifier: 1 part by weight of alkylaryl polyglycol ether To produce a suitable preparation of active compound, 1 part by weight of active compound is mixed with the stated amounts of solvents and emulsifier, and the concentrate is diluted with water to the desired concentration.

To test for protective activity, young plants are sprayed with the preparation of active compound at the stated application rate. After the spray coating has dried on, the plants are inoculated with an aqueous spore suspension of *Sphaeroth-*

*eca fuliginea*. The plants are then placed in a greenhouse at about 23° C. and a relative atmospheric humidity of about 70%.

Evaluation is carried out 7 days after the inoculation. 0% means an efficacy which corresponds to that of the control, whereas an efficacy of 100% means that no infection is observed.

Active compounds, application rates and test results are shown in the table below.

TABLE A

| Ex. | Active compound | Active compound application rate in g/ha | % efficacy |
|---|---|---|---|
| 4 | [structure] | 100 | 100 |
| 6 | [structure] | 100 | 100 |
| 1 | [structure] | 100 | 100 |
| 2 | [structure] | 100 | 95 |

Example B

*Venturia* Test (Apple)/Protective

Solvents: 24.5 parts by weight of acetone
24.5 parts by weight of dimethylacetamide
Emulsifier: 1.0 part by weight of alkylaryl polyglycol ether To produce a suitable preparation of active compound, 1 part by weight of active compound is mixed with the stated amounts of solvents and emulsifier, and the concentrate is diluted with water to the desired concentration.

To test for protective activity, young plants are sprayed with the preparation of active compound at the stated application rate. After the spray coating has dried on, the plants are inoculated with an aqueous conidia suspension of the apple scab pathogen *Venturia inaequalis* and then remain in an incubation cabin at about 20° C. and 100% relative atmospheric humidity for one day.

The plants are then placed in a greenhouse at about 21° C. and a relative atmospheric humidity of about 90%.

Evaluation is carried out 10 days after the inoculation. 0% means an efficacy which corresponds to that of the control, whereas an efficacy of 100% means that no infection is observed.

TABLE B

| Ex. | Active compound | Active compound application rate in g/ha | % efficacy |
|---|---|---|---|
| 4 | [structure] | 100 | 99 |
| 1 | [structure] | 100 | 100 |

Example C

*Botrytis* Test (Bean)/Protective

Solvents: 24.5 parts by weight of acetone
24.5 parts by weight of dimethylacetamide
Emulsifier: 1.0 part by weight of alkylaryl polyglycol ether To produce a suitable preparation of active compound, 1 part by weight of active compound is mixed with the stated amounts of solvents and emulsifier, and the concentrate is diluted with water to the desired concentration.

To test for protective activity, young plants are sprayed with the preparation of active compound at the stated application rate. After the spray coating has dried on, 2 small pieces of agar colonized by *Botrytis cinerea* are placed onto each leaf. The inoculated plants are placed in a dark chamber at about 20° C. and 100% relative atmospheric humidity.

2 days after the inoculation, the size of the infected areas on leaves is evaluated. 0% means an efficacy which corresponds to that of the control, whereas an efficacy of 100% means that no infection is observed.

TABLE C

*Botrytis* test (bean)/protective

| Ex. | Active compound | Active compound application rate in g/ha | % efficacy |
|---|---|---|---|
| 4 | (structure) | 500 | 94 |
| 1 | (structure) | 500 | 98 |

Example D

*Alternaria* Test (Tomato)/Protective

Solvent: 49 parts by weight of N,N-dimethylformamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young tomato plants are sprayed with the preparation of active compound at the stated application rate. 1 day after the treatment, the plants are inoculated with an aqueous spore suspension of *Alternaria solani* and then remain at 100% relative humidity for 24 hours. The plants then remain at about 96% relative atmospheric humidity and a temperature of 20° C.

Evaluation is carried out 7 days after the inoculation. 0% means an efficacy which corresponds to that of the control, whereas an efficacy of 100% means that no infection is observed.

Active compounds, application rates and test results are shown in the table below.

TABLE D

*Alternaria* test (tomato)/protective

| Ex. | Active compound | Active compound application rate in g/ha | % efficacy |
|---|---|---|---|
| 4 | (structure) | 750 | 95 |

The invention claimed is:
1. A thiazolylbiphenylamide of the formula (I)

(I)

in which
  $R^1$, $R^2$, $R^3$, $R^4$, and $R^5$ independently of one another represent hydrogen, halogen, cyano, nitro, $C_1$-$C_6$-alkyl, $C_2$-$C_6$-alkenyl, $C_1$-$C_4$-alkoxy, $C_1$-$C_4$-alkylsulfonyl, or $C_3$-$C_6$-cycloalkyl; or represent $C_1$-$C_4$-haloalkyl, $C_1$-$C_4$-haloalkoxy, $C_1$-$C_4$-haloalkylthio, or $C_1$-$C_4$-haloalkylsulfonyl having in each case 1 to 5 halogen atoms,
  $R^6$ represents $C_1$-$C_8$-alkyl, $C_1$-$C_6$-alkylsulfinyl, $C_1$-$C_6$-alkylsulfonyl, $C_1$-$C_4$-alkoxy-$C_1$-$C_4$-alkyl, $C_3$-$C_8$-cycloalkyl; represents $C_1$-$C_6$-haloalkyl, $C_1$-$C_4$-haloalkylsulfanyl, $C_1$-$C_4$-haloalkylsulfinyl, $C_1$-$C_4$-haloalkylsulfonyl, halo-$C_1$-$C_4$-alkoxy-$C_1$-$C_4$-alkyl, or $C_3$-$C_8$-halocycloalkyl having in each case 1 to 9 fluorine, chlorine, and/or bromine atoms; or represents —$CH_2NR^{10}R^{11}$, and
  $R^{10}$ and $R^{11}$ independently of one another represent hydrogen, $C_1$-$C_8$-alkyl, or $C_3$-$C_8$-cycloalkyl; or represent $C_1$-$C_8$-haloalkyl or $C_3$-$C_8$-halocycloalkyl having in each case 1 to 9 fluorine, chlorine, and/or bromine atoms.

2. A thiazolylbiphenylamide of formula (I) as claimed in claim 1 in which
  $R^1$, $R^2$, $R^3$, $R^4$, and $R^5$ independently of one another represent hydrogen, fluorine, chlorine, bromine, cyano, nitro, methyl, ethyl, n- or isopropyl, n-, iso-, sec-, or tert-butyl, methoxy, ethoxy, methylthio, ethylthio, n- or isopropylthio, cyclopropyl, trifluoromethyl, trichloromethyl, trifluoroethyl, difluoromethoxy, trifluoromethoxy, difluorochloromethoxy, trifluoroethoxy, difluoromethylthio, difluorochloromethylthio, or trifluoromethylthio, $R^6$ represents $C_1$-$C_6$-alkyl, $C_1$-$C_4$-alkylsulfinyl, $C_1$-$C_4$-alkylsulfonyl, $C_1$-$C_3$-alkoxy-$C_1$-$C_3$-alkyl, or $C_3$-$C_6$-cycloalkyl; represents $C_1$-$C_4$-haloalkyl, $C_1$-$C_4$-haloalkylsulfanyl, $C_1$-$C_4$-haloalkylsulfinyl, $C_1$-$C_4$-haloalkylsulfonyl, halo-$C_1$-$C_3$-alkoxy-$C_1$-$C_3$-alkyl, $C_3$-$C_6$-halocycloalkyl having in each case 1 to 9 fluorine, chlorine, and/or bromine atoms, or represents —$CH_2NR^{10}R^{11}$, and $R^{10}$ and $R^{11}$ independently of one another represent hydrogen, $C_1$-$C_6$-alkyl, or $C_3$-$C_6$-cycloalkyl; or represent $C_1$-$C_4$-haloalkyl or $C_3$-$C_6$-halocycloalkyl having in each case 1 to 9 fluorine, chlorine, and/or bromine atoms.

3. A thiazolylbiphenylamide of formula (I) as claimed in claim 1 in which $R^1$, $R^2$, $R^3$, $R^4$, and $R^5$ independently of one another represent hydrogen, fluorine, chlorine, bromine, cyano, methyl, methoxy, methylthio, trifluoromethyl, difluoromethoxy, trifluoromethoxy, difluoromethylthio, or trifluoromethylthio, $R^6$ represents methyl, ethyl, n- or isopropyl, n-, iso-, sec-, or tert-butyl, pentyl, or hexyl, methylsulfinyl, ethylsulfinyl, n- or isopropylsulfinyl, n-, iso-, sec-, or tert-butylsulfinyl, methylsulfonyl, ethylsulfonyl, n- or isopropylsulfonyl, n-, iso-, sec-, or tert-butylsulfonyl, methoxymethyl, methoxyethyl, ethoxymethyl, ethoxyethyl, cyclopropyl, cyclopentyl, cyclohexyl, trifluoromethyl, trichloromethyl, trifluoroethyl, difluoromethylsulfanyl, difluorochloromethylsulfanyl, trifluoromethylsulfanyl, trifluoromethylsulfinyl, trifluoromethylsulfonyl, trifluoromethoxymethyl, or —$CH_2NR^{10}R^{11}$, and $R^{10}$ and $R^{11}$ independently of one another represent hydrogen, methyl, ethyl, n- or isopropyl, n-, iso-, sec-, or tert-butyl, methoxymethyl, methoxyethyl, ethoxymethyl, ethoxyethyl, cyclopropyl, cyclopentyl, cyclohexyl; trifluoromethyl, trichloromethyl, trifluoroethyl, or trifluoromethoxymethyl.

4. A thiazolylbiphenylamide of formula (I) as claimed in claim 1 in which four of the radicals $R^1$, $R^2$, $R^3$, $R^4$, and $R^5$ represent hydrogen.

5. A thiazolylbiphenylamide of formula (I) as claimed in claim 1 in which $R^1$, $R^2$, $R^4$, and $R^5$ each represent hydrogen, and $R^3$ represents hydrogen, halogen, cyano, nitro, $C_1$-$C_6$-alkyl, $C_2$-$C_6$-alkenyl, $C_1$-$C_4$-alkoxy, $C_1$-$C_4$-alkylsulfonyl, or $C_3$-$C_6$-cycloalkyl; or represents $C_1$-$C_4$-haloalkoxy, $C_1$-$C_4$-haloalkylthio, or $C_1$-$C_4$-haloalkylsulfonyl having in each case 1 to 5 halogen atoms.

6. A thiazolylbiphenylamide of formula (I) as claimed in claim 1 in which $R^2$, $R^4$, and $R^5$ each represent hydrogen, and $R^1$ and $R^3$ independently of one another represent hydrogen, halogen, cyano, nitro, $C_2$-$C_6$-alkenyl, $C_1$-$C_4$-alkoxy, $C_1$-$C_4$-alkylthio, $C_1$-$C_4$-alkylsulfonyl, or $C_3$-$C_6$-cycloalkyl; or represent $C_1$-$C_4$-haloalkyl, $C_1$-$C_4$-haloalkoxy, $C_1$-$C_4$-haloalkylthio, or $C_1$-$C_4$-haloalkylsulfonyl having in each case 1 to 5 halogen atoms.

7. A thiazolylbiphenylamide of formula (I) as claimed in claim 1 in which $R^1$, $R^4$, and $R^5$ each represent hydrogen, and $R^2$ and $R^3$ independently of one another represent hydrogen, halogen, cyano, nitro, $C_2$-$C_6$-alkenyl, $C_1$-$C_4$-alkoxy, $C_1$-$C_4$-alkylthio, $C_1$-$C_4$-alkylsulfonyl, or $C_3$-$C_6$-cycloalkyl; or represent $C_1$-$C_4$-haloalkyl, $C_1$-$C_4$-haloalkoxy, $C_1$-$C_4$-haloalkylthio, or $C_1$-$C_4$-haloalkylsulfonyl having in each case 1 to 5 halogen atoms.

8. A thiazolylbiphenylamide of formula (I) as claimed in claim 1 in which $R^1$, $R^3$, and $R^5$ each represent hydrogen, and $R^2$ and $R^4$ independently of one another represent hydrogen, halogen, cyano, nitro, $C_2$-$C_6$-alkenyl, $C_1$-$C_4$-alkoxy, $C_1$-$C_4$-alkylthio, $C_1$-$C_4$-alkylsulfonyl, or $C_3$-$C_6$-cycloalkyl; or represent $C_1$-$C_4$-haloalkyl, $C_1$-$C_4$-haloalkoxy, $C_1$-$C_4$-haloalkylthio, or $C_1$-$C_4$-haloalkylsulfonyl having in each case 1 to 5 halogen atoms.

9. A thiazolylbiphenylamide of formula (I) as claimed in claim 1 in which $R^6$ represents methyl, ethyl, n- or isopropyl, n-, iso-, sec-, or tert-butyl, methylsulfinyl, methylsulfonyl, methoxymethyl, ethoxyethyl, cyclopropyl, cyclopentyl, cyclohexyl, trifluoromethyl, trichloromethyl, trifluoromethylsulfanyl, trifluoromethylsulfinyl, trifluoromethylsulfonyl, or trifluoromethoxymethyl.

10. A process for preparing a thiazollylbiphenylamide of formula (I) as claimed in claim 1 comprising reacting a thiazolylbiphenylamide of formula (II)

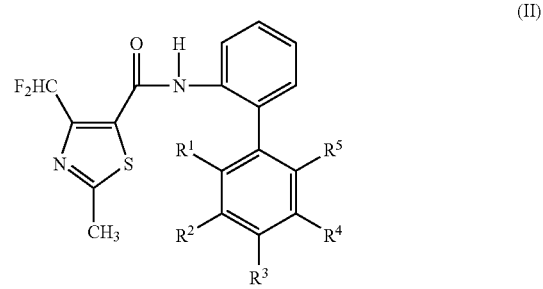

(II)

in which $R^1$, $R^2$, $R^3$, $R^4$, and $R^5$ are as defined for formula (I) in claim 1, with a halide of formula (III)

$R^6$—X (III)

in which $R^6$ is as defined for formula (I) in claim 1, and

X represents chlorine, bromine, or iodine, in the presence of a base and in the presence of a diluent.

11. A composition for controlling unwanted phytopathogenic fungi comprising one or more thiazolylbiphenylamides of formula (I) as claimed in claim 1 and one or more extenders and/or surfactants.

12. A method of controlling unwanted phytopathogenic fungi comprising applying an effective amount of one or more thiazolylbiphenylamides of formula (I) according to claim 1 to the fungi and/or their habitat.

13. A process for preparing compositions for controlling unwanted phytopathogenic fungi comprising mixing one or more thiazolylbiphenylamide of formula (I) as claimed in claim 1 with one or more extenders and/or surfactants.

* * * * *